United States Patent [19]

Oczkowski

[11] 4,359,051

[45] Nov. 16, 1982

[54] OSTOMY APPLIANCE CLOSURE

[75] Inventor: Boguslaw Oczkowski, Spotswood, N.J.

[73] Assignee: Johnson & Johnson Products, Inc., New Brunswick, N.J.

[21] Appl. No.: 239,860

[22] Filed: Mar. 2, 1981

[51] Int. Cl.³ .............................................. A61F 5/44
[52] U.S. Cl. .................................................... 128/283
[58] Field of Search .................. 128/283, 272, 214 D, 128/DIG. 24

[56] References Cited

U.S. PATENT DOCUMENTS

| | | | |
|---|---|---|---|
| 3,762,412 | 10/1973 | Frank | 128/283 |
| 3,906,951 | 9/1975 | Chen | 128/283 |
| 3,964,485 | 6/1976 | Neumeier | 128/283 |

FOREIGN PATENT DOCUMENTS 7811362 11/1978 France ................................ 128/283

Primary Examiner—Richard J. Apley
Assistant Examiner—T. J. Wallen

[57] ABSTRACT

Ostomy appliance having improved features for maintaining positive seal while being worn comprises mating cylindrical connectors on a base to be affixed to the ostamate and on the collection bag to be affixed to the base so proportioned that pressures created by body movements of the wearer tend to enhance rather than cause separation of the seal between the cylindrical connectors. In a preferred embodiment, hanger means are provided for both facilitating proper alignment and mating of the cylindrical connectors and for preventing accidental dropping of the collection bag.

4 Claims, 9 Drawing Figures

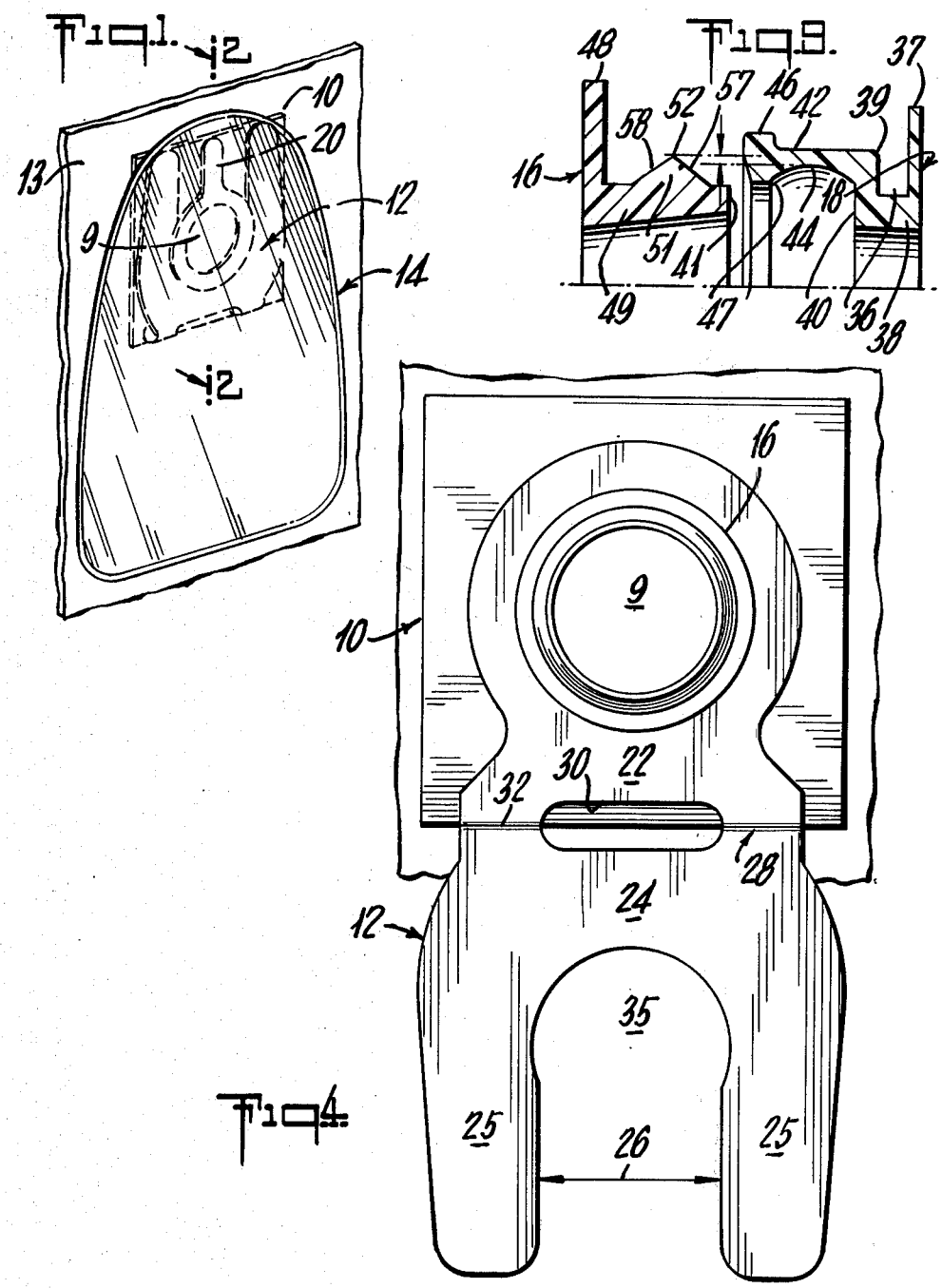

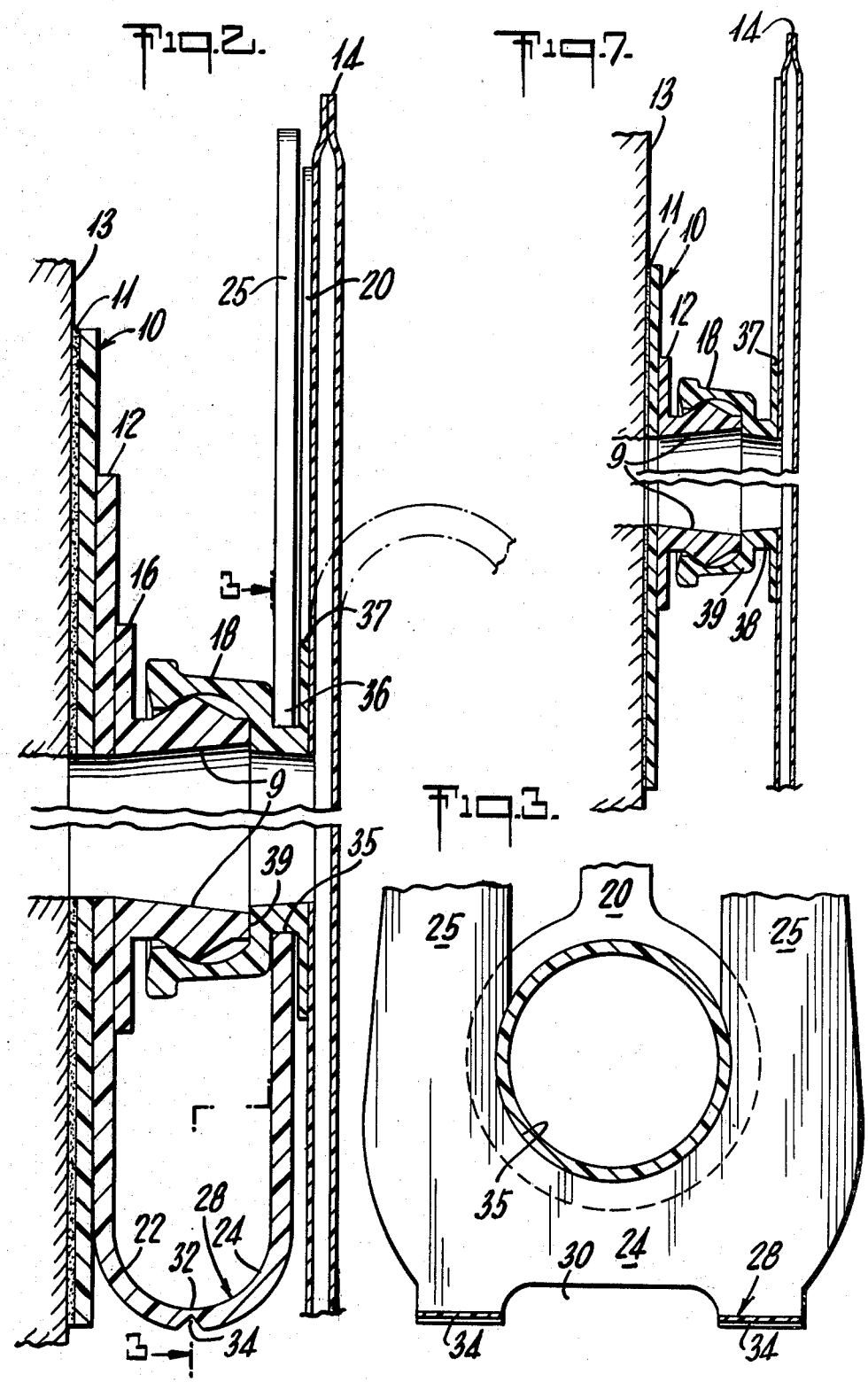

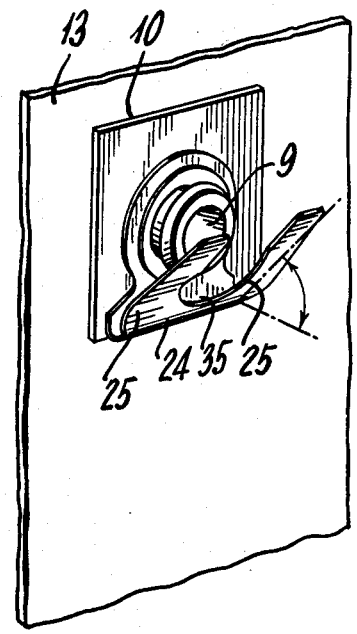
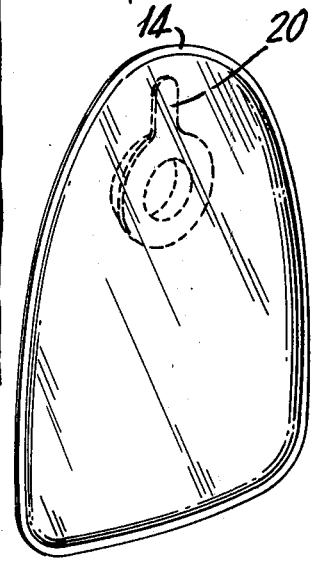
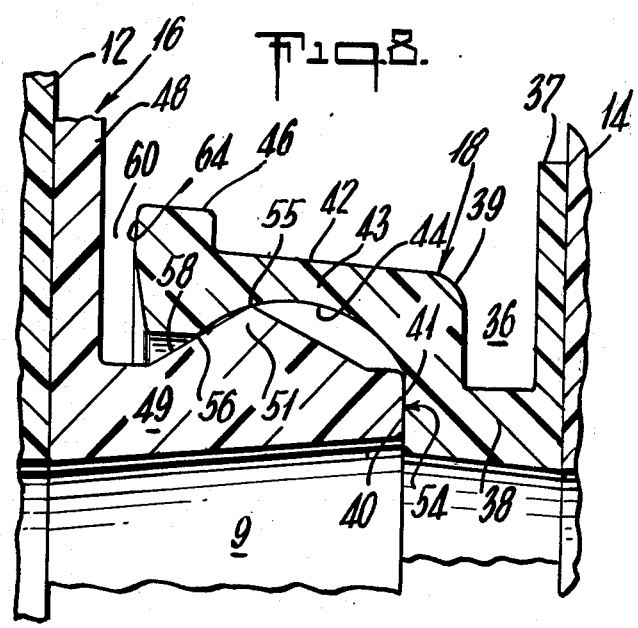

OSTOMY APPLIANCE CLOSURE

BACKGROUND OF THE INVENTION

1. Field of the Invention

This invention relates to an ostomy appliance having a superior closure device for preventing inadvertent leakage of gas, liquid or solid therefrom. In another embodiment, the invention also relates to means for facilitating proper closure of said closure device as well as for preventing dropping of said appliance when said closure device is in the open position.

A colostomy is the surgical creation of a new opening for the colon on the surface of the body, while an ileostomy is the surgical creation of an opening for the ileum. In an ileostomy the entire colon, the rectum, and sometimes a small portion of the ileum, is removed. In a colostomy the rectum, and sometimes a portion of the colon, is removed.

Both ileostomy and colostomy operations involve the creation of an artificial opening (stoma) in the abdomen to which the distal end of the healthy intestine is attached. Generally, the stoma is placed low on the abdomen and to one side. A related enterostomy for which the present invention might be useful is the urinary diversion. It involves the formation of a permanent fistula through which the ureter may discharge its contents.

2. Description of the Prior Art

U.S. Pat. No. 3,906,951, issued Sept. 23, 1975, to Chen James Ling, discloses an ostomy device for use by ostamates that comprises a disposable bag, a base designed to be adhesively secured to the skin of the patient surrounding the stoma, and means for releasably securing the bag to the base. This patent is directed to dealing with several problems that commonly have been associated with the use of such devices. These include seepage around the stoma, which in turn results in both skin irritation and at least partial destruction of the adhesive bond, as well as inadvertent disconnection between the bag and the base. The patent is primarily concerned with the seepage problem (which is dealt with by use of a hydrocolloid ointment around the stoma), but also discloses several means for connecting the bag to the base, including an elastic band and a particular flange arrangement described in detail at column 1, line 65, to Column 2, line 16, of the patent, which arrangement appears to involve a conventional male/female sealing ring connection. The device described in this patent appears to be the same as one being marketed by E. R. Squibb & Sons, Inc. under the trademark SUR-FIT. Another patent to the same patentee that describes generally the use of adhesive means to attach a disposable bag to a base (or directly to the skin) surrounding a stoma in U.S. Pat. No. 3,941,133, issued Mar. 2, 1976.

SUMMARY OF THE INVENTION

The present invention is concerned with improved means for positively securing a bag to a base of an ostomy device in such manner as to avoid inadvertent detachment, affording confidence to the user that embarrassing accidents will not occur, while at the same time facilitating easy removal of the bag when desired.

In accordance with the present invention there is provided an ostomy appliance comprising a collection bag or similar means for receiving effluent from the stomal opening of an ostamate and a base adapted to be secured to the body of said ostomate adjacent said stomal opening and to be releasably connected to the collection bag while providing fluid communication between the stomal opening and collection bag wherein the collection bag comprises a liquid impervious material having an opening therein and a first generally annular collar means symetrically aligned about an axis extending from said opening, the base comprises second generally annular collar means symetrically aligned about said axis and adapted for insertion partially into the space defined within said first collar means and including a portion thereof remaining outside said space and a flexible radially extending flange disposed circumferentially about the portion of said second collar remaining outside the space defined by said first collar, the flange being spaced axially apart from the confronting end of said first annular collar means, and including adhesive or other means for securing the base to the body of the ostamate, and sealing means are cooperatively disposed on the confronting surfaces of said first and second collar means for providing a liquid impermeable seal therebetween, the flange extending a sufficient radial distance beyond the outer periphery of said first annular collar means such that in response to an axial force on said flange in a direction toward said first collar means, said flange will deflect into engagement with the end of said first collar means and produce a force tending to tighten the sealing action of said cooperative sealing means.

In accordance with an optional embodiment there is further provided support means fixed to the base for receiving the collection bag and facilitating proper alignment between the first and second collar means, the support means comprising a first flexible planar section fixed to the base flange, a second flexible planar section extending upwardly at an angle from the bottom of, but integral with, said first section, means for maintaining the angle of opening between first and second planar sections at between about 35° and 45° when no external force is applied thereto, and cut out means on the second section for receiving the first collar means in tight fitting relation at a level on said second section so selected that when the tight fitting relation is achieved, the first and second collar means are properly aligned for achieving the liquid impermeable seal.

BRIEF DESCRIPTION OF THE DRAWINGS

A preferred ostomy appliance in accordance with the present invention will now be described, by way of example, with reference to the accompanying drawings, in which:

FIG. 1 is a perspective view of the presently preferred ostomy appliance;

FIG. 2 is a cross-section taken along lines 2—2 of FIG. 1;

FIG. 3 is a cross-section, taken along lines 3—3 of FIG. 2, showing the connection between the bag flange and the bag holder of the appliance of FIG. 1;

FIG. 4 is a plan view of the bag holder of the appliance of FIG. 1 in the 180° (flat) open position;

FIG. 5 is a perspective view of the bag portion of the appliance of FIG. 1 showing the bag connector and its associated tab;

FIG. 6 is a perspective view of the base connector portion of the appliance of FIG. 1 showing the bag support holder in the normal (35°–45°) open position;

FIG. 7 is a cross-section similar to FIG. 2 showing an alternative ostomy appliance in accordance with the present invention that does not employ the bag support shown in FIGS. 1-4;

FIG. 8 is a detail view of a portion of the cross-sectional view of FIG. 7, showing the mating between the base connector and the bag connector; and FIG. 9 is a cross-section similar to FIG. 8 but showing the closure device in the open position.

In the drawings, like reference numerals indicate the same or similar parts.

DESCRIPTION OF THE PREFERRED EMBODIMENTS

Referring to FIGS. 1 and 2, the ostomy appliance comprises a base 10, a bag support 12 and a collection bag 14 which, when assembled and secured, surrounds the user's stoma and by means of common central opening 9 provides fluid communication between the stoma and bag 14. One side of base 10 comprises adhesive material 11 (FIG. 2) for securing base 10 to the skin 13 of the user and preventing leakage from opening 9. Affixed to the other side of base 10, by adhesive or other suitable conventional means, are bag support 12 and base connector 16. A bag connector 18, affixed to a convenient surface of bag 14 by heat sealing or other conventional means, is designed to interlock or mate with base connector 16 so as to securely connect bag 14 to base 10. Integral with bag connector 18 is a tab 20, which is an optional, preferred feature for facilitating both connection and disconnection between connectors 16 and 18. Tab 20 is particularly useful for disconnecting the bag 14 from base 10 and permits the user to avoid awkward pulling on the bag with the attendant risk of accidental breakage.

Referring particularly to FIGS. 2-6, bag support 12 comprises a pair of substantially flat sections 22, 24 that are essentially parallel in the closed position and are preferably formed from a single sheet of semi-rigid material such as polyethylene (or another suitable thermoplastic material). As best shown in FIG. 4, in which bag support 12 is shown fully opened (to a 180° angle of opening between sections 22 and 24) sections 22 and 24 are joined by a living hinge 28 constructed in the central portion of the sheet by means of a cut-out 30 about fold line 32, and V-shaped notches 34 (FIG. 3). Notches 34 are so designed as to limit the normal angle of opening between sections 22 and 24 to between about 35° and 45°. (See FIG. 6). Section 22 is the portion of support 12 that is fixed to base 10 (or, in an optional construction—not shown—to base connector 16). Section 24 comprises a pair of projections or arms 25 that define a U-shaped guide and support for bag connector 18. To facilitate proper mating between base connector 16 and bag connector 18, it is a particularly preferred feature of section 24 that it contains an inner circular cut-out 35, the diameter of which is greater than the distance 26 between arms 25 but is only slightly greater than the diameter of projection 38 (described below) of bag connector 18.

The closure device of the present invention is best illustrated in FIGS. 7-9, although it is also shown in the illustration of FIG. 2. This closure device is a snap-on seal element comprising cylindrical male connector 16 and corresponding female connector 18 for mating therewith. While these two connector elements obviously can be interchanged, in the preferred, illustrated embodiment, female connector 18 is affixed to ostomy bag 14 and male connector 16 is affixed to base 10. Referring particularly to FIGS. 8 and 9, in cross-section bag connector 18 comprises at its back end a flange 37 that is connected to bag 14 by heat sealing or other convenient means. Projecting from flange 37 towards the front of connector 18 is a cylindrical element or projection 38, the front end of which includes a lip 39 which serves to define a groove 36 between lip 39 and flange 37. The front edge of projection 38 defines a first contact surface 40 designed to provide a sealing surface for mating with a corresponding surface 41 at the front end of base connector 16. Projecting frontward from lip 39 is a cylindrical element 42 having an arcuate inner surface 44 and terminated at the front end of connector 18 with a lip portion 46 of substantially thicker cross section than that of wall 43 of cylinder 42.

Referring still to FIGS. 8 and 9, the male portion of the closure device of the invention, base connector 16, includes a back end sealing element, in the illustrated embodiment a separate flange 48. Projecting frontward from flange 48 is a cylindrical element 49, the outer surface of which comprises an angular or conical projection 51, which is so proportioned that when the facing surfaces 40, 41 of connectors 16, 18 are in contact to form a seal 54, the apex 52 (FIG. 9) of projection 51 is in contact with arcuate surface 44 of connector 16 to form a second seal at 55, while a third seal is simultaneously effected at 56 between the lower, inner edge 47 of lip portion 46 of connector 18 and the inside angular wall 58 of projection 51. The slope of outside wall 57 of projection 51 may vary considerably, but is conveniently so selected as to facilitate the passing of lip portion 46 over projection 51 when connectors 16, 18 of the snap-on closure device of the invention are connected.

Referring particularly to FIG. 8, an important feature of the illustrated preferred construction of the closure device is the provision of space 60 between the outer edge 64 of lip 46 of connector 18 and flange 48 of connector 16. This serves to prevent inadvertent disconnection which might otherwise occur when the sealing surface (and thus flange 48) of connector 16 is flexed due to body movements of the wearer. By virtue of this construction, any contact that does occur between flange 48 and female connector 18 will be at a point high on edge 64 of lip 46 whereby any pressure thus exerted on lip 46 will serve to enhance rather than to separate the seal at all three sealing surfaces, 54, 55, 56.

To use the illustrated, preferred embodiment of FIGS. 1-6, base 10 is adhesively affixed to the skin 13 by means of adhesive layer 11, with central opening 9 surrounding the stoma of the user. At this time, bag support 12 is in the normal open position illustrated in FIG. 6. Bag 14 is then secured to base 10 as follows. Bag connector 18 is positioned between arms 25 of guide 24 such that groove 36 receives arms 25. Connector 18 is then slid down within guide 24 until seated in circular cut-out 35. By virtue of the construction of cut-out 35 described above, connector 18 "snaps" into place, generally audibly, and is held there under the moderate pressure created by the complementary design of guide 24 and connector 18.

Bag support 12 is so constructed that when guide 24 is moved to the closed position illustrated in FIG. 1 with bag 14 secure in place as described above, base connector 16 and bag connector 18 are properly aligned to effect the seal described above. Again, as guide 24 is closed and thus brought into overlying relationship with section 22 of bag support 12, an audible "snap" is generally heard as the seal is effected between connectors 16 and 18. While the audible "snaps" are merely an inherent consequence of proper alignment, they afford an important psychological benefit to the user by thus assuring the user that proper alignment and a secure seal have been achieved.

In addition to providing the guide feature described above, which assists in properly and securely affixing the bag 14 to the base 10, bag support 12 affords the additional important advantage of preventing accidental dropping of the bag 14 either by virtue of inadvertant separation of connectors 16 and 18 while the bag 14 is being worn by the user or during intentional separation while removing the bag. Thus, the hinge construction of guide 12 serves to secure the bag 14 to base 10 even when connectors 16 and 18 are separated.

While the foregoing features of bag support 12 are obviously advantageous, they are preferred features that are not essential to the coupling device of the present invention. Thus, as indicated previously and as best illustrated with reference to FIGS. 7-9, the connection achieved by virtue or the construction of connectors 16, 18 is significantly superior to that provided by state-of-the art devices and provides adequate security to the user even when preferred bag support 12 is eliminated from the appliance. That is, the seals effected at 54, 55, 56 so complement and enhance each other that significant force and attention are required to disconnect the bag 14 from the base 10, so that such disconnection is quite unlikely to occur inadvertently. As will be apparent from the foregoing description, elimination of bag support 12 does away with the need or purpose for groove 36 in the construction of bag connector 18.

As will be apparent to those skilled in the art, and as indicated above, many modifications and variations of the foregoing detailed description are possible within the spirit and scope of the present invention.

Having thus described my invention, what I desire to secure by Letters Patent is defined in the appended claims.

What is claimed is:

1. An ostomy appliance comprising collection means for receiving effluent from the stomal opening of an ostomate; and a base adapted to be secured to the body of said ostomate adjacent said stomal opening and to be releasably connected to said collection means while providing fluid communication between said stomal opening and said collection means;

said collection means comprising a liquid impervious container having an opening therein, and a first generally annular collar means symmetrically aligned about an axis extending from said opening;

said base comprising a second generally annular collar means symmetrically aligned about said axis and adapted for insertion partially into the confines of said first collar means with a portion thereof remaining outside the confines of said first collar means, and a flexible radially extending flange disposed circumferentially about the portion of said second collar means remaining outside the confines of said first collar means, said flange being spaced axially apart from the confronting end of said first annular collar means;

sealing means cooperatively disposed on the confronting surfaces of said first and second collar means for providing a liquid impermeable seal therebetween;

said flange extending a sufficient radial distance beyond the outer periphery of said first annular collar means such that in response to an axial force on said flange in a direction toward said first collar means, said flange will deflect into engagement with said confronting end of said first collar means and produce a force tending to tighten the sealing action of said cooperative sealing means, and means on said flange for securing said base to the body of said ostomate.

2. The appliance of claim 1 wherein said cooperatively disposed sealing means includes an abutment surface extending generally radially from the inside of said first annular collar means into said collar means wall;

an arcuate recess extending axially along and circumferentially about the interior surface of said first annular collar means for said radially extending abutment surface to a point spaced apart from the end of said first annular collar means;

a generally planar surface extending axially along the interior wall of said first annular collaar means from the end of said arcuate recess to the end of said first annual collar means and extending circumferentially thereabout;

said second annular collar means including a cooperating radially extending abutment surface adapted to fit securely against said abutment surface of said first annular collar means; and a generally triangular bearing portion extending circumferentially about the outside surface of said second annular collar;

whereby two point sealing engagement between the confronting surfaces of said first and second annular collar is accomplished at one point by the engagement of the apex of said triangular bearing surface and said arcuate recess and at a second point by the engagement of said triangular bearing surface and the interior surface of said first collar at a location between said apex and the radially extending flange on said second collar.

3. The appliance of claim 1 wherein the interior surface of said second collar tapers radially outwardly in a direction from said flange to the free end of said second collar.

4. The appliance of claim 1 further comprising support means fixed to said base for receiving said container and facilitating proper alignment between said first and second collar means;

said support means comprising a first flexible planar section fixed to said base flange, a second flexible planar section extending upwardly at an angle from the bottom of, but integral with, said first section, means for maintaining said angle of opening between said first and second planar sections at between about 35° and 45° when no external force is applied thereto, and cut out means on said second section for receiving said first collar means in tight fitting relation at a level on said second section so selected that when said tight fitting relation is achieved, said first and second collar means are properly aligned for achieving said liquid impermeable seal.

* * * * *